United States Patent
Tokumoto et al.

(10) Patent No.: US 7,479,129 B2
(45) Date of Patent: Jan. 20, 2009

(54) INTERLABIAL PAD

(75) Inventors: Megumi Tokumoto, Kanonji (JP); Satoshi Mizutani, Kanonji (JP); Wataru Yoshimasa, Kanonji (JP)

(73) Assignee: Uni-Charm Corporation, Shikokuchuo-Shi, Ehime-Ken (JP)

(*) Notice: Subject to any disclaimer, the term of this patent is extended or adjusted under 35 U.S.C. 154(b) by 0 days.

(21) Appl. No.: 11/302,653

(22) Filed: Dec. 13, 2005

(65) Prior Publication Data

US 2006/0142726 A1    Jun. 29, 2006

(30) Foreign Application Priority Data

Dec. 28, 2004  (JP) .............................. 2004-381475

(51) Int. Cl.
  *A61F 13/15* (2006.01)
(52) U.S. Cl. ............... 604/385.16; 604/385.11; 604/385.201; 604/385.22; 604/385.17; 604/385.26
(58) Field of Classification Search ............ 604/385.01, 604/385.17, 385.18, 385.16, 385.21, 385.03, 604/385.04, 385.11, 385.22, 385.201, 385.26
  See application file for complete search history.

(56) References Cited

FOREIGN PATENT DOCUMENTS

| JP | 2004-097693 A | 4/2004 |
| JP | 2004-121611 A | 4/2004 |
| JP | 2004-261231 A | 9/2004 |
| WO | WO-98/57608 A1 | 12/1998 |
| WO | WO 9901093 * | 1/1999 |
| WO | WO-02/094149 A1 | 11/2002 |
| WO | WO-02/094153 A1 | 11/2002 |
| WO | WO-02/094156 A1 | 11/2002 |
| WO | WO-02/094161 A1 | 11/2002 |
| WO | WO-02/100315 A1 | 12/2002 |

* cited by examiner

*Primary Examiner*—Jacqueline F. Stephens
(74) *Attorney, Agent, or Firm*—Darby & Darby P.C.

(57) ABSTRACT

An interlabial pad can maintain a state of constant contact with the inner walls of the labia and prevent leakage and falling away, regardless of changes in the position of the wearer. According to an interlabial pad having a pair of strip-shaped areas extending toward the side-edges along the center axis from the center axis and a low flexural rigidity part in the region including at least the side-edge out of the strip-shaped area, a state of constant contact with the inner walls of the labia can be maintained and leakage and falling away can be prevented, regardless of changes in position of the wearer.

13 Claims, 10 Drawing Sheets

INTERLABIAL PAD

This application is based on and claims the benefit of priority from Japanese Patent Application No. 2004-381475, filed on 28 Dec. 2004, the content of which is incorporated herein by reference.

BACKGROUND OF THE INVENTION

1. Field of the Invention

The present invention relates to an interlabial pad which can maintain a state of constant contact with the inner walls of the labia, regardless of changes in the position of the wearer, and prevent leakage and falling away.

2. Related Art

Conventionally, sanitary napkins and tampons are generally used as feminine catamenial products. Here, with regards to sanitary napkins, significant efforts have been made to prevent leakage of menstrual blood from gaps created by weak contact in the vicinity of the ostium vaginae. Furthermore, with regard to tampons, significant efforts have been made to eliminate foreign-body sensations and discomfort while inserted and difficulty in insertion into the vagina, arising from the attributes of the products.

Under these conditions, interlabial pads (hereinafter, "pads") have been receiving attention in recent years as a catamenial product which is halfway between a sanitary napkin and a tampon. This interlabial pad is worn by inserting one part thereof between a woman's labia and enabling it to come into contact with the inner surface of the labia. It is sanitary and clean since leakage of menstrual blood can be prevented because it is in closer contact to the body, compared to a sanitary napkin, and in addition, menstrual blood can be prevented from spreading and widely contacting the body. In addition, because it is smaller than sanitary napkins, it is superior in comfort when in use and causes less psychological resistance to wearing compared to tampons which are inserted into the vagina.

However, because interlabial pads are worn on the body by the holding force between the labia, it must flexibly follow the movements of the left and right labia which are generated by the movements of the wearer. If the interlabial pad has difficulty following body movements, there is risk of it falling away from the labia of the wearer. Therefore, various interlabial pads which can come into closer contact with the body have been studied.

The interlabial pad described in Patent Reference 1 is formed from a liquid permeable top sheet, a slightly liquid permeable back surface sheet and an absorbent member placed therebetween and preferably includes a folding axis along the center line in the longitudinal direction of the interlabial pad. By being folded along this folding axis and inserted into the labia of the wearer, the top sheet of the pad maintains contact with the inner walls of the labial of the wearer and, because it has a uniform covered range, falling away can be prevented.

Patent Reference 1: Japanese Patent Application Publication No. 2001-506168.

However, the interlabial pad described in Patent Reference 1 has a uniform thickness aside from the center line in the longitudinal direction which is the folding axis and the flexural rigidity of the pad is uniform. Therefore, if pressure is applied to a part of the pad from the leg (thigh) or buttocks, accompanying changes in the position of the wearer (walking, or positions such as sleeping positions on one's side), this force is transmitted to the entire pad. Furthermore, a pad which is held between the labia may become misaligned and there is a risk of the interlabial pad falling away from the labia.

In addition, because the interlabial pad described in Patent Reference 1 has almost uniform flexural rigidity, if an even greater force is applied, the pad buckles and bends significantly. If the pad is bent, because the inner wall of the labia is pressed by the pad section which has buckled, the labia is deformed and a space is formed between the interlabial pad and the inner walls of the labia. Therefore, the force holding the interlabial pad is weakened and there arises a risk of the interlabial pad falling away from the labia.

SUMMARY OF THE INVENTION

The present invention has been made in view of the above problems, and an object of the invention is to provide an interlabial pad which can maintain a state of constant contact with the inner walls of the labia, regardless of changes in the position of the wearer, and prevent leakage and dropping.

In order to solve the above problems, the inventors of the present invention have conducted intensive research, focusing on the necessity for accommodating the pressure applied to the pad. As a result, it was discovered that a state in which the inner walls of the labia and the pad are in constant contact can be maintained, regardless of the changes in the position of the wearer, by suppressing the diffusion of force applied from the side surface of the pad to the entire pad with the changes in the position of the wearer by providing a low flexural rigidity part which preferentially bends easily, and the present invention was thereby completed. More specifically, the present invention provides the following.

(1) An elongated interlabial pad including: an absorbent member for absorbing and retaining body fluid; a central folding axis parallel to a longitudinal direction passing through a lateral center of the interlabial pad; a pair of strip-shaped areas each extending from the central folding axis towards a side-edge roughly parallel to the central folding axis; and a pair of low flexural rigidity parts each of which is disposed in each of the strip-shaped areas in proximity to the side edge.

The interlabial pad in (1) has a pair of strip-shaped areas which extend from the central folding axis towards the side-edges parallel to the central folding axis of the pad, and an area including at least one of the side-edges, out of these strip-shaped areas, includes a low flexural rigidity part. By providing a particular part of the pad with a low flexural rigidity part in this way, the low flexural rigidity part preferentially bends and compensates for pressure even when pressure is applied to the side-surface of the pad, and therefore, pressure is not transmitted over the entire pad and the pad does not buckle. In addition, the pad does not become twisted when in use and leakage and falling away of the pad due to gaps forming between the inner walls of the labia and the pad can be prevented.

(2) The interlabial pad according to (1), in which the strip-shaped areas are provided at a slant towards a front-side of the interlabial pad, at an angle of 10 degrees or more and 90 degrees or less to the central folding axis.

In the interlabial pad in (2), the strip-shaped areas are provided at a slant towards a front-edge of the interlabial pad, that is to say, a front-side of the wearer, at an angle of 10 degrees or more and 90 degrees or less, more preferably at an angle of 30 or more and 60 or less to the central folding axis. The strip-shaped areas as such, which is provided at such an angle, follow the outer shape of the labia minora of the wearer when it is worn. The strip-shaped areas as such, which are provided to follow the outer shape of the labia minora, receive pressure easily by changes in the position of the wearer, and with the interlabial pad in (2), the low flexural rigidity part is placed in this part which receives pressure easily. Therefore, according to the interlabial pad in (2), the formation of gaps between the inner walls of the labia and the pad due to twisting and the like during wear can be prevented, and leakage and falling away of the pad can be prevented effectively.

(3) The interlabial pad according to (1) or (2), in which the absorbent member includes a pair of first parts each of which is positioned in each of said low flexural rigidity parts and a second part having a lower flexural rigidity than that of the first parts; in which the value of flexural rigidity B of each of the first parts is smaller than the value of flexural rigidity B of the second part; and in which the difference is $0.1 \times 10^{-4}$ (N·m$^2$/m) or more and $5.0 \times 10^{-4}$ (N·m$^2$/m) or less.

The interlabial pad in (3) is designed such that the value of flexural rigidity B of each of the first parts of the absorbent member positioned in the low flexural rigidity part is less than the second part of the absorbent member positioned in its vicinity. "Flexural rigidity B" is a value measured in compliance to the measuring method by the KES system, and more particularly, the difference between the value of flexural rigidity B of each of the first parts of the absorbent member positioned in the low flexural rigidity part and the value of flexural rigidity B of the second part the absorbent member positioned in the vicinity of the low flexural rigidity part is $0.1 \times 10^{-4}$ (N·m$^2$/m) or more and $5.0 \times 10^{-4}$ (N·m$^2$/m) or less. In addition, it is more preferably $0.5 \times 10^{-4}$ (N·m$^2$/m) or more and $2.0 \times 10^{-4}$ (N·m$^2$/m) or less. According to the interlabial pad in (3) as such, the low flexural rigidity part bends preferentially and accommodates pressure even when pressure is applied to the pad, and leakage and falling away of the pad can be prevented effectively.

(4) The interlabial pad according to any one of (1) to (3), n which the absorbent member includes a pair of first parts each of which is positioned in each of said low flexural rigidity parts and a second part having a lower flexural rigidity than that of the first parts; in which the basis weight per unit area in the first part is less than the basis weight per unit area in the second part, and in which the difference is 20 g/m$^2$ or more and 1000 g/m$^2$ or less.

The interlabial pad in (4) is designed such that the basis weight per unit area of each of the first parts of the absorbent member positioned in the low flexural rigidity part is less than that of the second part of the absorbent member positioned in its vicinity. More specifically, the difference between the basis weight per unit area of each of the first parts of the absorbent member positioned in the low flexural rigidity part and the basis weight per unit area of the second part of the absorbent member positioned in the vicinity of the low flexural rigidity part is 20 g/m$^2$ or more and 1000 g/m$^2$ or less. In addition, it is more preferably 100 g/m$^2$ or more and 500 g/m$^2$ or less. Because the interlacing of fibers is reduced and density is reduced by setting the basis weight per unit area of a part of the absorbent member to a small value, a low flexural rigidity part can be formed. Therefore, the interlabial pad in (4) is one in which low flexural rigidity part is formed by adjusting the basis weight per unit area of the absorbent member, and according to this interlabial pad in (4), the above effects can be realized.

(5) The interlabial pad according to any one of (1) to (4), in which the absorbent member has a slit in the low flexural rigidity part.

In the interlabial pad in (5), a slit is provided in the absorbent member in the low flexural rigidity part. By providing a slit, bending to the central folding axis direction is facilitated and the low flexural rigidity part can be formed. Therefore, the interlabial pad in (5) is one in which the low flexural rigidity part is formed by providing a slit, and according to this interlabial pad in (5), the above effects can be realized.

(6) The interlabial pad according to any one of (1) to (5), in which the absorbent member includes fibers, a pair of first parts each of which is positioned in each of said low flexural rigidity parts and a second part having a lower flexural rigidity than that of the first parts; and in which 5% or more fibers included in the first part have larger fiber diameters than fiber diameters of fibers included in the second part.

In the interlabial pad in (6), 5% or more of fibers forming the first part of the absorbent member positioned in the low flexural rigidity part are fibers with large fiber diameters. Because fibers with large fiber diameters are not easily interlaced and the distance between fibers is large, the low flexural rigidity part can be formed. Therefore, the interlabial pad in (6) is one in which the low flexural rigidity part is formed by adjusting the diameter of the fiber used in each of the first parts of the absorbent member, and according to this interlabial pad in (6), the above effects can be further realized.

(7) The interlabial pad according to any one of (1) to (6), in which emboss treatment is performed on the absorbent member, in which the absorbent member includes a pair of first parts each of which is positioned in each of said low flexural rigidity parts and a second part having a lower flexural rigidity than that of the first parts embossing treatment is performed on the absorbent member, the embossed-area ratio of the first part is smaller than the embossed-area ratio of the second part, and the difference is 0.5% or more and 40% or less.

In the interlabial pad in (7), embossing treatment is performed on the absorbent member and, in addition, the pad is designed such that the embossed-area ratio of each of the first parts of the absorbent member positioned in the low flexural rigidity part is smaller than that of the second part of the absorbent member positioned in its vicinity. More specifically, the difference between the embossed-area ratio of each of the first parts of the absorbent member positioned in the low flexural rigidity part and the embossed-area ratio of the second part of the absorbent member in the vicinity of the low flexural rigidity part is 0.5% or more and 40% or less. In this way, the low flexural rigidity part can be formed by making the embossed-area ratio small. Therefore, the interlabial pad in (7) is one in which the low flexural rigidity part is formed by adjusting the embossed-area ratio, and according to this interlabial pad in (7), the above effects can be sufficiently realized.

(8) The interlabial pad according to any one of (1) to (7) in which: the absorbent member is placed between a liquid permeable surface side sheet and a back face sheet; and the stress of the front surface sheet in the low flexural rigidity part is 0.01 N/25 mm or more and 0.5 N/25 mm or less when stretched 5% in the direction roughly parallel to the central folding axis, when stretched with gripping interval of 100 mm and tensile rate of 100 m/min.

The interlabial pad in (8) has a part of the front surface sheet positioned in the low flexural rigidity part has significant expandability in the central folding axis direction. More particularly, the part of the front surface sheet positioned in the low flexural rigidity part is designed such that the stress when stretched 5% in the central folding axis direction is 0.01 N/25 mm or more and 0.5 N/25 mm or less, when stretched with gripping interval of 100 mm and tensile rate of 100 m/min. By giving a significant expandability in the central folding axis direction to at least a part of the front surface sheet in this way, bending of the pad to the central folding axis direction is facilitated and the low flexural rigidity part can be formed. Therefore, the interlabial pad in (8) is one in which the low flexural part is formed by giving a significant expandability in the central folding axis direction to at least a part of the front surface sheet, and the above effects can be sufficiently realized.

(9) The interlabial pad according to (8) in which the stress of the back face sheet in the low flexural rigidity part is 0 N/25 mm or more and 1.5 N/25 mm or less when stretched 3% in a direction roughly parallel to the central folding axis, when stretched with gripping interval of 100 mm and tensile rate of 100 m/min.

The interlabial pad in (9) has a part of the back face sheet positioned in the low flexural rigidity part has significant expandability in the longitudinal direction. More particularly, the part of the back face sheet positioned in the low flexural rigidity part is designed such that the stress when stretched 3% in the central folding axis direction is 0 N/25 mm or more and 1.5 N/25 mm or less, when stretched with gripping interval of 100 mm and tensile rate of 100 m/min. By giving a significant expandability in the central folding axis direction to at least a part of the back face sheet in this way, bending of the pad to the central folding axis direction is facilitated and the low flexural rigidity part can be formed. Therefore, the interlabial pad in (9) is one in which the low flexural part is formed by giving the back face sheet significant expandability in the central folding axis direction, and according to this interlabial pad in (9), the above effects can be sufficiently realized.

(10) The interlabial pad according to any one of (1) to (9) in which: the absorbent member is placed between a liquid permeable surface side sheet and a back face sheet; the low flexural rigidity part includes a cut out portion which extends toward the central folding axis from the side-edge; and the cut out portion has a predetermined width and does not reach the central folding axis.

In the interlabial pad in (10), a cut out portion which extends toward the central folding axis extends from one of the side-edges which is parallel to the central folding axis of the absorbent member, but does not reach the central folding axis, is provided. This cut out portion has a predetermined width, does not reach the central folding axis, and divides the pad, excluding the vicinity of the central folding axis, into two. By providing a cut out portion as such, the tip in the vertical direction of the front part and the back part of the pad when in use can be bent in differing horizontal directions. Therefore, even when the tip part of the labia minor moves horizontally with the changes in the position of the wearer and the front part and the back part of the pad is slightly twisted in differing horizontal directions, the linear shape of the central folding axis of the pad can be maintained. At the same time, the tip part of the pad in the vertical direction can twist according to the slight contortion of the labia. In addition, because the central folding axis of the pad can maintain a linear shape, a state in which the central folding axis of the pad is in contact with the linear vestibular floor within the labia can be maintained, and furthermore, because the tip part of the pad in the vertical direction can bend horizontally according to the slight contortion of the labia, gaps are not formed between the inner wall of the labia and the pad, and close contact between the labia and the pad can be maintained. As a result, the pad can be prevented from falling away from the labia, and leakage of menstrual blood from gaps can be prevented.

(11) The interlabial pad according to (10), in which the cut out portion is provided only on the absorbent member.

In the interlabial pad in (10), the cut out portion which extends toward the central folding axis extends from the side-edge is provided only on the absorbent member and is not provided on the front surface sheet and the back surface sheet. By providing a cut out portion as such, bending of the pad to the central folding axis direction is facilitated and the low flexural rigidity part can be obtained. Therefore, the interlabial pad in (11) is one in which the low flexural rigidity part is formed by providing a cut out portion only on the absorbent member, and according to this interlabial pad in (11), the above effects can be sufficiently realized.

(12) The interlabial pad according to any one of (1) to (11), in which the length from the central folding axis to the side-edges is smaller in the back-side than the front-side of the interlabial pad.

In the interlabial pad in (12), the length from the central folding axis to the side-edges is designed to be smaller in the back-side of the interlabial pad disposed in the back-side of the wearer than the length from the central folding axis to the side-edge in the front-side, when in use. The labia minora tends to extend more in the vertical direction in the front-side of the wearer than the back-side, and the back-side of the pad is easily exposed from the labia and easily buckled in the central folding axis direction, compared to the front-side. Therefore, according to the interlabial pad in (11), by shortening the length from the central folding axis to the side-edge in the back-side of the pad and reducing the areas exposed from the labia, buckling of the pad in the central folding axis direction can be prevented and the above effects can be sufficiently realized.

According to the present invention, an interlabial pad which can maintain a state of constant contact with the inner walls of the labia, regardless of the changes in the position of the wearer, and prevent leakage and falling away can be provided.

DETAILED DESCRIPTION OF THE INVENTION

The embodiments of the present invention are described below, with reference to the drawings. In explanations of respective embodiments other than the first embodiment, the same reference numbers are affixed and explanations thereof are omitted or simplified with regards to those shared with the first embodiment.

First Embodiment

Overall Construction of the Interlabial Pad

Figure 1:
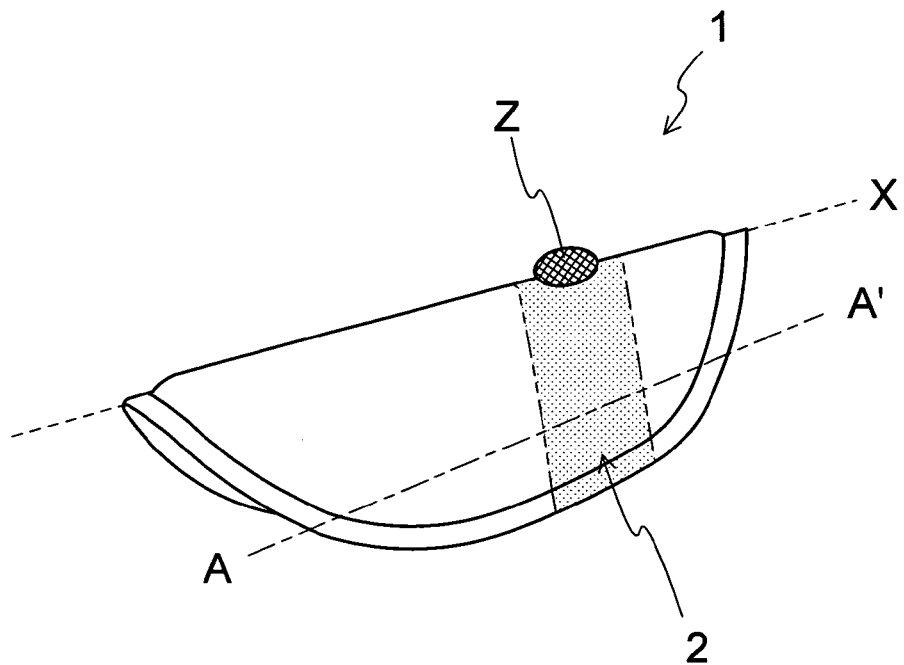
FIG. 1 is a perspective view of a flattened interlabial pad 1 which is folded into two.

FIG. 1 shows a perspective view of interlabial pad 1 according to this embodiment. The interlabial pad 1 is a substantially oval plate having a surface which is longer in a direction parallel to a central folding axis (hereinafter called "central folding axis direction") X than in a lateral direction roughly perpendicular to the central folding axis. The interlabial pad 1 is folded with the central folding axis as the folding line and is worn such that at least a part is held between the labia minora so that at least a part in the vicinity of the central folding axis contacts the vestibular floor within the labia of a wearer. The interlabial pad 1 has a pair of strip-shaped areas which extends towards the side-edges, the side-edges are parallel to the central folding axis, and in an area of each of the strip-shaped areas, the area includes at least one of the side-edges of these strip-shaped areas, includes a low flexural rigidity part 2 which has lower flexural rigidity than its surrounding areas is disposed.

Shapes which are suitable for the female labia, such as an ellipsoid, an hour-glass-shape, and a teardrop-shape, are given as shapes of the interlabial pad 1. The length of the outer form of the interlabial pad 1 is preferably 40 to 180 mm, as the length in the central folding axis direction x and is more preferably 80 to 120 mm. In addition, the width in the lateral direction perpendicular to the central folding axis is preferably 20 to 100 mm and more preferably 50 to 80 mm. This width in the lateral direction perpendicular to the central folding axis is the length of the interlabial pad 1 in a flat, before being folded in half. When the interlabial pad 1 being folded in half is worn between the labia, the length in the vertical direction, in the wearing state, is roughly ½ of the above width. Although the interlabial pad 1 is a type in which a flat pad is folded in half and held between the labia, as stated above, it can also have a shape having a thickness in the vertical direction such as a rod shape or a cylindrical shape. In interlabial pads other than the type which is worn by folding a flat pad in half, the width in the lateral direction perpendicular to the central folding axis is roughly ½ of the above width.

The average length of the pudendal slit (from the front labial commissural part to the back labial commissural part) is approximately 80 mm, the average length from the clitoris to the ostium vaginae is approximately 40 mm, and the average length from the ostium vaginae to the anus is approximately 45 mm (researched by the applicant). The front side-edge of the interlabial pad preferably extends to cover up to at least the clitoris in order to prevent leakage of menstrual blood, and the back side-edge preferably does not reach the anus, in order to prevent the pad from falling away due to movement of the buttocks muscles. It is desirable that the lengths of the outer form of the interlabial pad be within the above range, as the range to fulfill these conditions.

Figure 2:
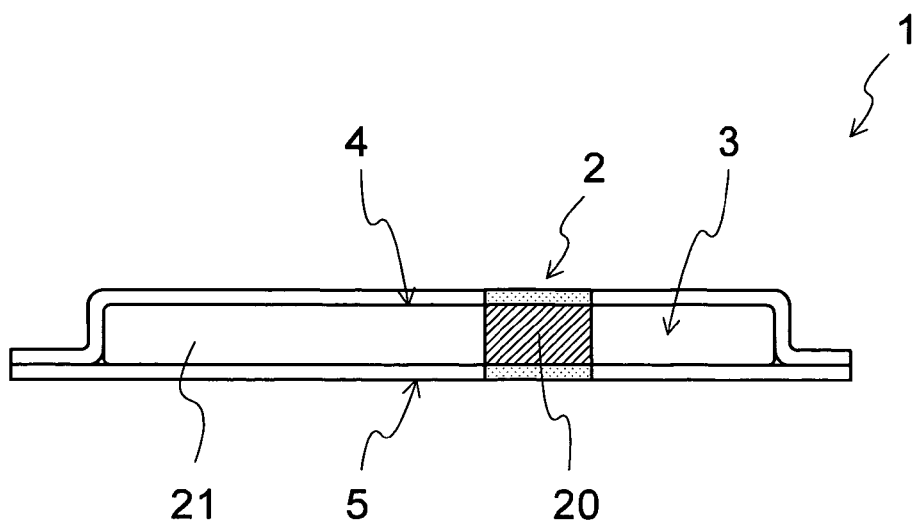
FIG. 2 is an A-A' cross-sectional view of the interlabial pad 1 in FIG. 1.

FIG. 2 is a cross-sectional view of A-A' in FIG. 1. As shown in FIG. 2, the interlabial pad of the present embodiment includes an absorbent member 3, and a liquid-permeable front surface sheet 4 and a back surface sheet 5 to cover both surfaces of the absorbent member 3. The interlabial pad 1 has a pair of low flexural rigidity parts 2 each of which is formed by lowering the flexural rigidity of a part of the absorbent member 3. Specifically, a part of the absorbent member 3 positioned in each of the low flexural rigidity parts 2 is modified to have a lower flexural rigidity than another surrounding areas. Because the flexural rigidity of the interlabial pad 1 is changed by changing the flexural rigidity of the absorbent member 3, each of the low flexural rigidity parts 2 can be formed by lowering the flexural rigidity of a part of the absorbent member 3.

Absorbent Member 3

Pulp, chemical pulp, rayon, acetate, natural cotton, polymer absorbent material, fibrous polymer absorbent material, synthetic fibers, foam, and the like, for example, are given as materials for absorbent member 3 of the interlabial pad 1, and the materials can be used alone, or in combinations of at least two of them. Although the absorbent member 3 is not particularly limited as long as it can absorb and retain menstrual blood and the like, it is preferably bulky, capable of keeping its shape, and causes little chemical effects on the body. More specifically, bulky material is preferable so as to enable compression which does not cause foreign-body sensations to the wearer. Specifically, rayon and acetate which have been physically embossed, chemical pulp which has been cross-linked by cross-linking agent and crimped, or compound synthetic fibers and the like such as side-by-side types, biased core type of core-in-sheath, and core-in-sheath type which are formed by using the heat contraction rate of resin, such as polyethylene (PE), polypropylene (PP), polyethylene terephthalate (PET), and the like, can be used mainly. In addition, these compound synthetic fibers can be those in which the molecular orientation thereof is enhanced by stretching during fiber spinning or those in which differing cross-sectional shapes such as Y-shape and C-shape are combined. Furthermore, for the purpose of improving the sliding between fibers, an oil solution can be applied to or contained within the fibers forming the absorbent member 3. In addition, in order to enable the interlabial pad to be flushed by water, it can be water-degradable materials or biodegradable materials.

The absorbent member 3 disposed inside of the interlabial pad 1 can be obtained by opening and stacking these fibers.

The absorbent member 3 can be a type in which these fibers are stacked into a single layer, or a multi-layer type comprising high hydrophilic fiber on the bottom layer rather than the top layer in order to store the menstrual blood. The absorbent member 3 can be obtained by processing fiber into sheets by, for example, air-laid method, spun-lace method, papermaking method, melt-blown method and the like, and subsequently entwining fibers by performing needling processing. Alternatively, it can also be obtained by passing fibers which have been made into sheets between dot-shaped, lattice-shaped, wave-shaped, etc., rolls and embossing.

A part of Absorbent Member 3 Positioned in Low Flexural Rigidity Part 2

The absorbent member 3 has a first part 20 and a second part 21 having a different flexural rigidity from that of the first part. The first part 20 is disposed in a part corresponding to each of the low flexural rigidity parts 2 of the interlabial pad 1. The flexural rigidity of the first part 20 is lower than that of the second part 21 and the first part is a low flexural rigidity part of the absorbent member 3. The first part 20 is provided in an area including at least one of the side-edges in each of a pair of strip-shaped areas which extend from the central folding axis of the interlabial pad 1 towards the side-edges along the central folding axis. Generally, in many cases, the female labia minora is more developed in the vertical direction in the front part, rather than the back part, the average length of the front part of the labia minora (the halfway point on the clitoris-side when the distance between the clitoris and the ostium vaginae is divided into three equal parts) in the vertical direction is 14 mm, and the average length in the vicinity of the ostium vaginae is 3 mm (researched by the applicant). Therefore, when the interlabial pad 1 is worn, the interlabial pad 1 is prone to being exposed from the labia minora, from the vicinity of the ostium vaginae backwards. The front part of the interlabial pad, which is fitted in the labia minora, does not easily bend in the central folding axis direction X, because it is held by the labia minora. On the other hand, with the back part of the interlabial pad, which is exposed from the labia minor, external pressure is directly transmitted to the interlabial pad. Therefore, the flexibility of the front part of the interlabial pad, which is fitted in the labia minora, and the back part of the interlabial pad, which is exposed from the labia minora, differs, and the vicinity of the ostium vaginae contact part Z tends to cause bending. In the interlabial pad 1 of the present embodiment, the low flexural rigidity part 2 is provided in the pair of strip-shaped areas, including the vicinity of the ostium vaginae contact part Z which causes bending, which extends from the central folding axis towards the side-edges along the central folding axis.

The width of the low flexural rigidity part 2 is preferably 1 mm or more and 30 mm or less, and more preferably, 5 mm or more and 10 mm or less. If it is narrower than 1 mm, it cannot bend sufficiently with little force, and if it is wider than 30 mm, the pad becomes twisted during use.

In addition, it is preferable that the low flexural rigidity part 2 be provided between the ranges from the center point of central folding axis X of the interlabial pad 1 to the point 5 mm from the back side-edge of the interlabial pad 1. Because the low flexural rigidity part 2 is provided in the strip-shaped areas including the vicinity of the ostium vaginae contact part Z which causes bending, if this low flexural rigidity part Z is provided biased toward the front from the center point of central folding axis X, the front part of the interlabial pad will not cover the clitoris and the back part of the interlabial pad will reach the anus. In addition, if it is provided behind the 55 mm point of the back side-edge of interlabial pad 1, the menstrual blood flowing from the ostium vaginae will leak out of the back part of the interlabial pad. Value of Flexural Rigidity B of the Part of the Absorbent Member Positioned in the Low Flexural Rigidity Part 2

The value of flexural rigidity B of a part (the first part 20) of the absorbent member 3 positioned in the low flexural rigidity part 2 of the interlabial pad 1 according to the present embodiment is less than that of another part (the second part 21) of the absorbent member 3 positioned in areas surrounding the first part 20. The difference between the value of flexural rigidity B of the first part 20 of the absorbent member 3 and the value of flexural rigidity B of the second part 21 of the absorbent member 3 is preferably $0.1 \times 10^{-4}$ ($N \cdot m^2/m$) or more and $4.0 \times 10^{-4}$ ($N \cdot m^2/m$) or less. In addition, it is more preferably $0.5 \times 10^{-4}$ ($N \cdot m^2/m$) or more and $2.0 \times 10^{-4}$ ($N \cdot m^2/m$) or less. The value of flexural rigidity B is in compliance with the measurement method of the KES system, and is the value of a bending curvature of 0.2 $cm^{-1}$ (0.1 to 0.3 $cm^{-1}$), measured under the condition, 40 mm between chucks, using "KES Bending Tester" measuring equipment (KES-FB2-L), manufactured by Kato Tech. The measured width of the absorbent member as a measurement sample is 30 mm and the length in the chuck direction is about 80 mm.

Manufacturing Method of the Absorbent Member 3 Having the First Part 20

A method in which the basis weight per unit area of the first part 20 of the absorbent member 3 is made lower than the basis weight per unit area of the second part 21 of the absorbent member 3 and the thickness uniform, for example, is given as a method for providing the first part 20 to the absorbent member 3. Through this, the density of the first part 20 becomes lower than the density of the second part 21 surrounding the first part 20, and therefore, interlacing between fibers comprising the absorbent member 3 is reduced and the range in which the fibers can move is increased in the first part 20. Thus, the flexural rigidity of the first part 20 can be made lower than that of another surrounding area. In the present embodiment, the basis weight per unit area of the absorbent member 3 are changed between the first part 20 and the second part 21, and the difference between the basis weight per unit area of the first part 20 and the basis weight per unit area of the second part 21 is preferably 20 $g/m^2$ or more and 1000 $g/m^2$ or less. In addition, it is more preferably 100 $g/m^2$ or more and 500 g/m2 or less. If the difference between basis weights per unit area is less than 20 $g/m^2$, difference in rigidity to the degree that prioritized bending occurs is not attained, and if a difference of more than 1000 $g/m^2$ is set, the wearer will experience foreign-body sensations, which is not preferable.

As an example of an absorbent member 3, in which the first part 20 has been formed by being adjusted by the difference in basis weights per unit area, one in which a compound material of 85% rayon of 3.3 dtex and 15% cotton is used as the material forming the absorbent member 3, and is constructed such that the basis weight per unit area of the first part 20 is 100 $g/m^2$, and the basis weight per unit area of the second area 21 is 300 $g/m^2$ is given. As an example for lowering the basis weight per unit area, a process for stacking the compound material of 85% rayon of 3.3 dtex and 15% cotton such as to be 300 g/m and then partially loosening interaction between fibers by pulling the stacked compound material towards two opposing directions and until the basis weights per unit are of the stretched part becomes to be 100 $g/m^2$, is given.

Example of Flexural Rigidity B Measurement

An example of the measurement of the value of flexural rigidity B is shown below. In order to measure the value of flexural rigidity B of the first part 20 and the second part 21 of the absorbent member 3 separately, an absorbent member for measurement having the same structure as the first part 20 and another absorbent member for measurement having the same structure as the second part 21 were formed.

Absorbent Member for Measurement Having the Same Structure as the First Part 20

A compound material of 85% rayon of 3.3 dtex and 15% cotton was stacked such that basis weight per unit area becomes 360 g/m², onto a stack of a tissue of 15 g/m² basis weight per unit area and a spun-lace non-woven fabric of 45 g/m² basis weight per unit area composed of 70% rayon and 30% polyethylene terephthalate. Heat-embossing, using an embossing machine having a dotted embossing pattern with dots aligned with a distance of 12 mm between adjacent dots at an angle of 30° and having an area of 1 mm², was performed on the obtained stacked product to form a sample in which each layer is fixed. The sample was used as an absorbent member for measuring the flexural rigidity B of the second part 21.

Absorbent Member for Measurement Having the Same Structure as the First Part 20

The compound material of 85% rayon of 3.3 dtex and 15% cotton was stacked such that basis weight per unit area was 360 g/m², embossing using the embossing machine having a dotted pattern with dots aligned with a distance of 12 mm between adjacent dots at an angle of 30° and having an area of 1 mm², was performed, and a temporarily fixed pre-sample was obtained. The obtained pre-sample was stretched in opposite directions of the longitudinal direction, so that the basis weight per unit area thereof was adjusted to 180 g/m², and was placed on a tissue of 15 g/m² basis weight per unit area and a spun-less non-woven fabric of 45 g/m² basis weight per unit area composed of a compound material of 70% rayon and 30% polyethylene terephthalate, and then, fixed by the same embossing process as above to form a sample. The sample was used as an absorbent member for measuring the flexural rigidity B of the first part 20.

Measurement of the Value of Flexural Rigidity B

The flexural rigidity value B of respective samples was measured using a "KES Bending Tester" measuring equipment (KES-FB2-L), manufactured by Kato Tech. One example of the measurement results is shown in Table 1.

TABLE 1

|  | Main constituent material | Basis weight per unit area (g/m²) | Flexural rigidity value B (B: × 10⁻⁴ • Nm²/m) |
|---|---|---|---|
| Second Part | 85% 3.3 dtex rayon: 15% cotton | 360 | 1.404 |
| First Part | 85% 3.3 dtex rayon: 15% cotton | 180 | 0.415 |

Front Surface Sheet 4

As a material for a front surface sheet 4, a material which is liquid-permeable, hydrophilic, and does not irritate the skin is preferably used. For example, materials of one or more than two non-woven fabrics obtained from manufacturing methods, such as spun-less, point-bond, and through-air, are used. Among these materials, those which are mainly composed of cellulose fluid-hydrophilic fibers are preferable in order to prevent the wearer form feeling foreign-body sensations. In addition, they can be water-degradable materials and biodegradable materials to allow flushing.

Back Surface Sheet 5

A sheet of polyethylene, polypropylene, polyethylene terephthalate, polyvinyl alcohol, polylactic acid, and polybutylene succinate and the like having a thickness of 15 to 60 μm, a non-woven fabric, paper or a laminated sheet of the resins mentioned above, are given as materials for back surface sheet 5. In addition, an air-permeable film obtained by mixing an inorganic filler to a film raw material to form a film and stretching the obtained film can be also used. In particular, a film which is mainly composed of low-density polyethylene resin and adjusted to a range of 15 to 30 g/m² basis weight per unit area and, more particularly, air-permeable film adjusted to a hole-opening area rate of 10 to 30% and hole diameter within the range of 0.1 to 0.6 mm are given. Spun-bond non-woven fabric, point-bond non-woven fabric, through-air non-woven fabric and the like are given as examples of non-woven fabric, and water-repellant processing can be performed thereon. Among these, a SMS (spun-bond/melt-blown/spun-bond) non-woven fabric which includes melt-blown, comprising extra-fine fibers and having an extremely short distance between fibers, is preferable. In this case, it is preferably configured with basis weights per unit area within the range of 5 to 15 g/m² for the spun-bond layer, 1 to 10 g/m for the melt-blown layer, and 5 to 15 g/m² for the spun-bond layer. In addition, the back surface sheet 5 can be water-degradable materials and biodegradable materials to enable flushing.

Manufacturing Method for Interlabial Pad 1

The interlabial pad 1 of the present embodiment is obtained by joining an absorbent member 3, a front surface sheet 4, and a back surface sheet 5. A method in which the absorbent member 3, the front surface sheet 4, and the back surface sheet 5 are heat-sealed by applying heat when embossing, a method for joining with adhesive and the like, for example, are given as joining methods, and these methods can be used alone or in combination.

The embossed pattern when joining by embossing is not particularly limited and can be selected accordingly from dot-shape, lattice-shape, wave-shape and the like. Out of these, it is preferable to join with an area rate of 10% by dot-shape emboss pattern because this will not cause excessive foreign-body sensations to the inner walls of the labia.

When joining by heat-sealing, heat is applied at a temperature higher than the softening point of the constituent materials, and heat embossing, ultrasonic machining and the like can be given.

When joining with adhesive, a rubber-adhesive, such as SEBS, SBS, and SIS and the like, a pressure-sensitive adhesive or a heat-sensitive adhesive mainly composed of olefine series material, such as straight-chain low-density polyethylene, and a moisture-sensitive adhesive composed of water-soluble polymer, such as polyvinyl alcohol, carboxyl methylcellulose, and gelatin, or water-swelling polymer, such as polyvinyl acetate and sodium polyacrylate, are given as examples. Among these, heat-sensitive adhesives are preferable because, should the adhesive ever seep out to the outer surface of an interlabial pad when body pressure is applied thereto, it can be made so as to not have any tack properties at this point. As an example of a specific adhesive, that which is a melted mixture of 5 to 25% SEBS, 40 to 60% alicyclic hydrocarbon, 1 to 10% aromatic denatured terpene and 15 to 35% additives may be given.

As a coating pattern of the adhesive, spiral coating, control-seam coating, coater coating, curtain-coater coating, spray-gun coating and the like are given. In addition, the basis weight per unit area of the adhesive is preferably in the range of 1 to 30 g/m² and more preferably in the range of 3 to 10 g/m². If the pattern is one in which adhesive is coated linearly, the line diameter is preferably in the range of 30 to 300 μm. If the basis weight per unit area is less than 1 g/m², or if the line diameter is less than 30 μm, adhesive leaks between the fibers if the front surface sheet 4 is composed of fiber aggregate, and therefore, sufficient adhesive power cannot be obtained. On the other hand, if the basis weight per unit area is larger than 30 g/m², or if the line diameter is more than 300 μm, the border part of the portions to which adhesive has been applied becomes rigid. The coating location is not particularly limited, as long as it is applied to at least one portion of or the entire pad border. However, it is preferable that it be applied to the back surface side of the absorbent member and to at least one portion of or the entire boarder, taking in to consideration fluid absorbency.

Figure 3:
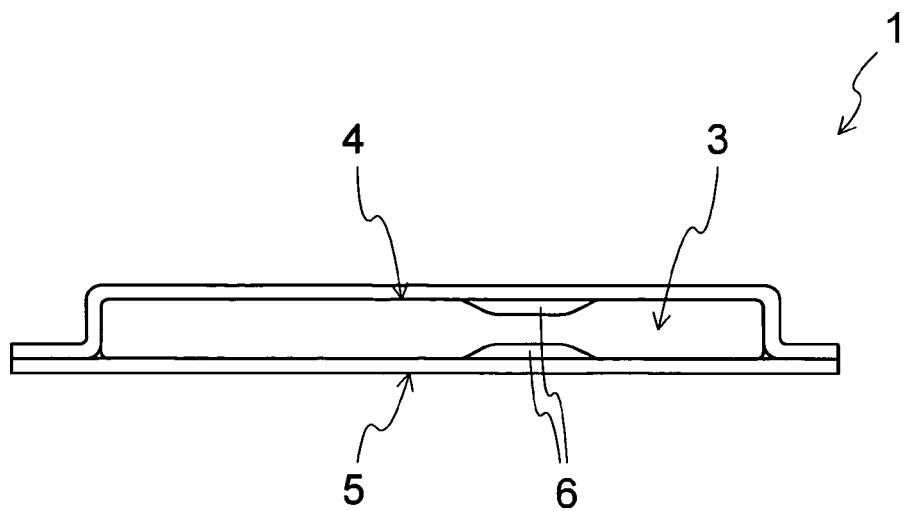
FIG. 3 is a diagram explaining a state in which front surface sheet 4 and back surface sheet 5 are not joined with absorbent member 3.

In addition, in the low flexural rigidity part 2, it is preferable that neither the front surface sheet 4 nor the back surface sheet 5 be joined to the absorbent member 3 (refer to FIG. 3). By providing space 6 between the absorbent member 3 and each sheet, the interlabial pad 1 is not prevented from being bent by the tension of the front surface sheet 4 and the back surface sheet 5 when the interlabial pad 1 is bent in the longitudinal direction Y, and bending can be facilitated.

Functions and Effects

In the interlabial pad 1 according to a first embodiment, by providing a low flexural rigidity part 2 with a lower rigidity than the surrounding part to the pair of strip-shaped areas extending from the central folding axis of the interlabial pad towards the side-edges along the central folding axis, bending can be facilitated selectively in the portions with low rigidity, regardless of whether force from the left-side or right-side in the horizontal direction is applied to the front part and the back part of the pad, and in addition, even if the force is minimal. Therefore, force is not transmitted to the entire pad and the pad does not buckle. In addition, because low rigidity portions are provided partially, the pad does not become twisted during use, the shape of the pad can be maintained, and buckling can be prevented. As a result, the generation of a space between the inner walls of the labia and the interlabial pad can be prevented, the pad can be maintained within the labia, and the falling away of the pad from the labia can be avoided.

Second Embodiment

Slit Processing of Absorbent Member 3a

Figure 4A:
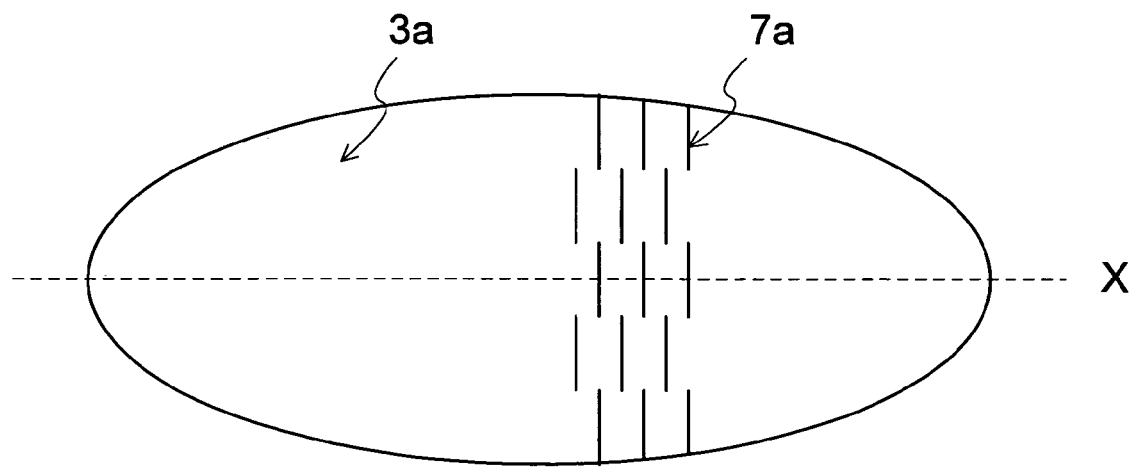
FIG. 4A is a top view of an absorbent sheet 3a according to a second embodiment.

FIG. 4A is a top view of an absorbent member 3a of a flat interlabial pad. The absorbent member 3a of the interlabial pad in FIG. 4A is one in which slits facing the direction perpendicular to the central folding axis are provided in the area (the first part) to become the low flexural rigidity part of the absorbent member 3a, in order to facilitate bending of interlabial pad in the central folding axis direction X, and constituents excluding this are the same as that of the first embodiment. In the second embodiment, the shape of slit 7a is not particularly limited and can be linear, curved, wavy, and the like. The length of one slit 7a is preferably within the range of 1 mm or more and 20 mm or less, and the distance between slits 7a is preferably within the range of 1 mm or more and 20 mm or less. Furthermore, the slit 7a according to the present invention may or may not penetrate the absorbent member 3a in the thickness direction.

The slit pattern according to the second embodiment can be a combination of slit patterns facing the direction perpendicular to the central folding axis and the slit patterns facing the central folding axis direction X, intersecting slit patterns, and furthermore, slit patterns to the diagonal direction. In the present embodiment, providing slit patterns facing the direction perpendicular to the central folding axis discontinuously in the direction perpendicular to the central folding axis and arranging such that portions with slit 7a and portions without appear alternately in the central folding axis direction X, as shown in FIG. 4, is preferable for both shape-retention of the absorbent member 3a and the formation of an area which bends preferentially.

Third Embodiment

Interlacing of Fibers in the Absorbent Member 3b

Figure 4B:
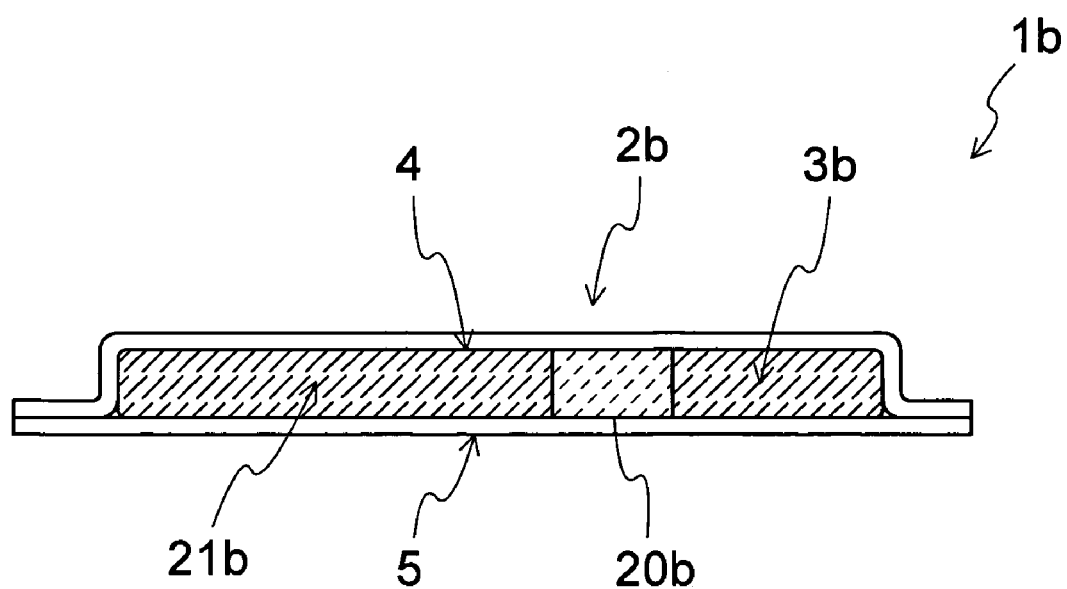
FIG. 4B is a cross-sectional view of an interlabial pad 1b according to a third embodiment.

FIG. 4B is a cross sectional view of an interlabial pad 1b according to a third embodiment cut along the central holding axis. The interlabial pad 1b of the third embodiment is one which uses material in which the fibers are not easily interlaced as material comprising a part (a first part) 20b of an absorbent member 3b, the part is positioned in the corresponding of the low flexural rigidity part 2b, and constituents excluding this are the same as that of the first embodiment. As materials, in which the fibers are not easily interlaced, fibers which contain a high percentage of thick denier fibers, for example, can be given. If the percentage of the thick denier fibers contained is high, the fibers become less prone to interlacing and the distance between the fibers becomes wider than that in the surrounding areas (the second part) 21b, and therefore, the flexural rigidity in the low flexural rigidity part 2b becomes low and the area of the low flexural rigidity part 2b can be bent preferentially. In addition, as material of which the fibers are not easily interlaced, fibers which have short fiber lengths are given. If fiber length is short, there is little interlacing between fibers, and flexural rigidity can be reduced. In the present embodiment, materials which contain 5% by mass or more of fibers with large fiber diameters are preferable as material in which the fibers are not easily interlaced. If the fiber with large fiber diameters is less than 5% by mass, difference in rigidity to the degree in which there is preferential bending cannot be attained.

As material including the first part 20b positioned in the low flexural rigidity part 2b, it is preferable that the percentage of material which tends to not retain menstrual blood when wet, compared to the surrounding areas, be high. If the percentage of material which tends to not retain menstrual blood when damp is high, fibers do not stick together even when wet, and bulkiness can be maintained, thereby maintaining low flexural rigidity.

As a specific example in the third embodiment, an example in which material which is collected at 300 g/m², after opening at a combination rate of 30% core-in-sheath, biased-core type synthetic fiber of 4.4 dtex PE and PP with fiber lengths of 51 mm, fiber crimping rate of 50%, and 0.2% application of hydrophilic oil and 70% 5.6dtex rayon with fiber length of 32 mm, fiber crimping rate of 50%, and 0.2% application of hydrophilic oil is used as the constituent material of low flexural rigidity part 2b, and that which is collected at 300 g/m², after opening at a combination rate of 85% 3.3 dtex rayon and 15% cotton is used as the constituent material of the surrounding areas is given.

Fourth Embodiment

Embossed-area Ratio of Absorbent Member 3c

Figure 4C:
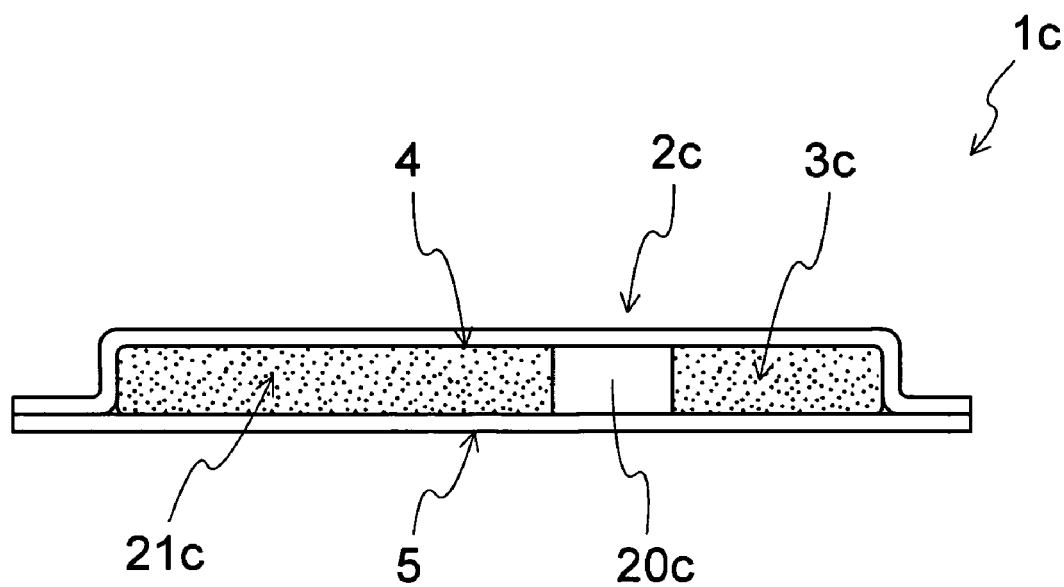
FIG. 4C is a cross-sectional view of an interlabial pad 1c according to a forth embodiment.

FIG. 4C is a cross sectional view of an interlabial pad 1c according to a fourth embodiment cut along the central holding axis. The interlabial pad 1c of the fourth embodiment is one in which an absorbent member 3c is embossed, and constituents excluding this are the same as that of the first embodiment. In the fourth embodiment, absorbent member 3c includes a first part 20c positioned in corresponding to the low flexural rigidity part 2c by adjusting the embossed-area ratio of the absorbent member 3c. In other words, the embossed-area ratio of the part of the absorbent member 3c positioned in the low flexural rigidity part 2c is set lower than the surrounding areas (the second part 21c). Because the difference in the embossed area becomes the difference in flexural rigidity, the areas with low embossed-area ratio tend to bend preferentially. As an example of embossed-area ratio adjustment, it is preferable that the embossed rate of the first part 20c positioned in the low flexural rigidity part 2c be within the range of 0 to 20%, the embossed rate of the surrounding area be 0.5% to 40%, and a difference of 0.5% or more and 40% or less between the embossed-area ratio of the first part 20c positioned in the low flexural rigidity part 2c and the surrounding area is provided. If the difference of the embossed-area ratio is less than 0.5%, difference in rigidity to the degree in which there is preferential bending cannot be attained, and if a difference which is larger than 40% is provided, the rigidity of the overall pad increases and the wearer experiences foreign-body sensations.

As a specific example of the present embodiment, a configuration in which an embossed part is not provided in the first part 20c positioned in the low flexural rigidity part 2c, dot-shaped embossing with an area of 1 mm² is adjacent to the surrounding area, and an embossed pattern consecutively aligning embossing processing part with a distance of 7 mm between adjacent embossing parts and an angle of 45° is given.

The processes according to the above embodiments can be used, alone or in combination, as methods for including low flexural rigidity part in the present invention.

Fifth Embodiment

Front Surface Sheet Positioned in the Low Flexural Rigidity Part

It is preferable that the front surface sheet has expansibility in at least the direction of the central folding axis, in order to not obstruct bending of the interlabial pad in the low flexural rigidity part in the central folding axis direction. The entirety of the front surface sheet may have expansibility in the direction of the central folding axis, or only a part positioned in the low flexural rigidity part may have the expansibility in the direction of the central folding axis.

Thermoplastic resin, such as polyethylene, polypropylene, and polyethylene terephthalate, can be given as materials for the part of the front surface sheet positioned in the low flexural rigidity part. The front surface sheet 4 can include, as materials, synthetic fiber using these resins alone or synthetic materials using these in compounds, such as core-in-sheath types and side-by-side types, and for example, non-woven fabrics in which these fiber sheets are water-interlaced or combined or used singly by spun-bond, through-air and the like can be given. In addition, it can include cellulose fluid-hydrophilic fibers such as pulp, chemical pulp, rayon, acetate, natural cotton and the like, when taking into consideration hydrophilic properties with bodily fluids. Particularly, spunlace non-woven fabric and expansible, spun-lace non-woven fabric, in which, after fibers combined with the percentages of 5 to 30% rayon or acetate and 70 to 95% polyethylene terephthalate are adjusted within the range of 20 to 60 g/m², fibers are interlaced by water-interlacing and dried, and adjusted to thickness within the range of 0.3 to 1.0 mm, are preferably used.

Stress of the Part of the Front Surface Sheet Positioned in Low Flexural Rigidity Part In the present invention, the stress of the front surface sheet in the low flexural rigidity part is preferably 0.01 N/25 mm or more and 0.5 N/25 mm or less when stretched 5% in the central folding axis direction, when stretched at low-speed, with gripping interval of 100 mm and tensile rate of 100 m/min. If the stress when stretched 5% in the central folding axis direction is less than 0.01 N/25 mm, it becomes difficult to maintain the shape as a sheet, and if it is more than 0.5 N/25 mm, the bending of the entire pad is obstructed because the front surface sheet is stretched when the pad tries to bend at the low flexural rigidity part.

Manufacturing Method of the Front Surface Sheet a Part of which is Positioned in the Low Flexural Rigidity Part and has Expansibility in the Direction of the Central Folding Axis The expansibility of the front surface positioned in the low flexural rigidity part can be increased by reducing the binding force between the fibers of the front surface sheet. If the binding force between fibers is reduced, the degree of freedom of each fiber increases, and therefore, fibers can move when the pad is folded in the longitudinal direction at the low flexural rigidity part and obstruction of the bending due to stretching of the front surface sheet can be prevented.

Figure 4D:
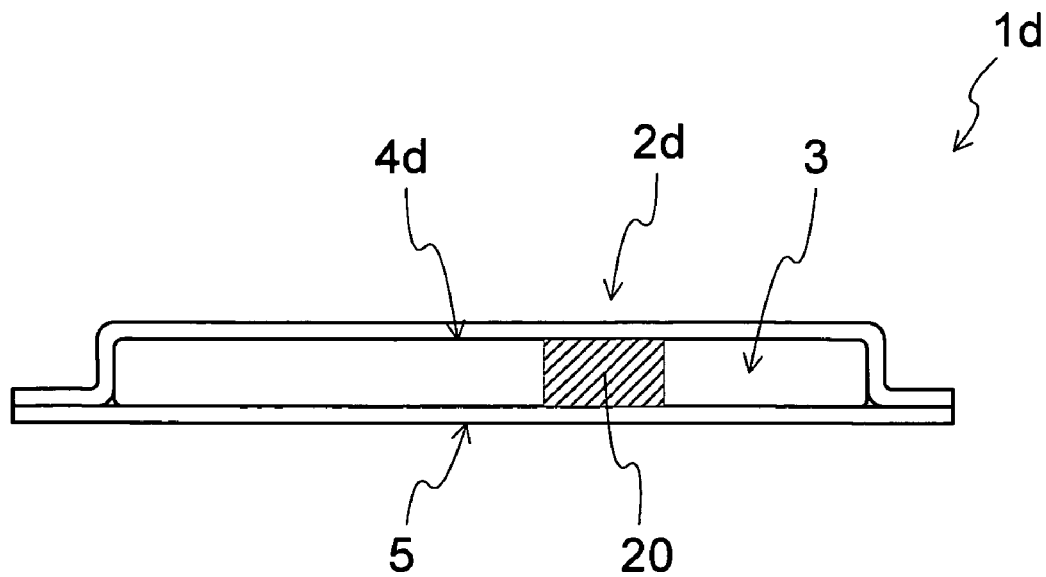
FIG. 4D is a cross-sectional view of an interlabial pad 1d according to a fifth embodiment.

FIG. 4D is a cross sectional view of an interlabial pad id according to a fifth embodiment cut along the central holding axis. The interlabial pad 1d according to the fifth embodiment is one which uses a sheet with weak binding force between fibers as a front surface sheet 4d so that the front surface sheet 4d can expand in the central folding axis direction in the low flexural rigidity part 2d, and constituents excluding this are the same as those in the first embodiment. In the fifth embodiment, the sheet having weak binding force between fibers can be given expansibility in the stage in which the sheet is formed. If the sheet is created by water-interlacing, binding force between fibers can be reduced by lowering the water pressure for interlacing fibers. When creating the front surface sheet 4d having an expandable part in the central folding axis used for the present embodiment, water pressure is preferably 4.9 mN/cm². If synthetic fibers are combined in the sheet, drying temperature is a temperature lower than that of the softening point of the synthetic fibers, in the drying process after water-interlacing.

Sixth Embodiment

Reducing Binding Force Between Fibers in the Front Surface Sheet 4e

Figure 4E:
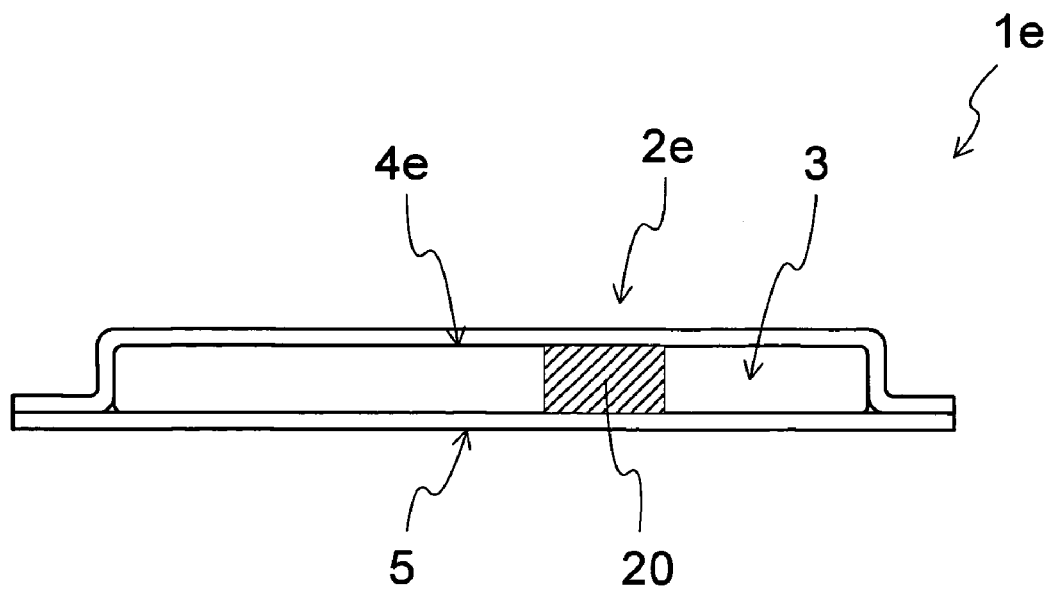
FIG. 4E is a cross-sectional view of an interlabial pad 1e according to a sixth embodiment.

FIG. 4E is a cross sectional view of an interlabial pad 1e according to a sixth embodiment cut along the central holding axis. The interlabial pad 1e in the sixth embodiment is one which uses a sheet which has be processed such that the binding force between fibers is weak as a front surface sheet 4e so that the front surface sheet 4e can expand in the central folding axis direction in the low flexural rigidity part, and constituents excluding this are the same as those in the first embodiment. In the sixth embodiment, processing for reducing the binding force between fibers is performing a process for reducing the binding force between fibers on at least a part of a front surface sheet with higher stress than 0.5 N/25 mm and poor expansibility. As processing methods performed in the front surface sheet with poor expansibility, a method for tendering at least a part of the front surface sheet and a method for performing wave-shaped embossing, after forming the front surface sheet 4e, are given. These processes can be performed on the entire front surface sheet, or can be performed on at least a part which is positioned on low flexural rigidity part 2e. The processes are preferably performed a region which is positioned on low flexural rigidity part 2e areas because the flatness of the front surface sheet contributes to retaining the shape of the front surface sheet and maintaining the adhesive properties of the inner walls of the labia and the front surface sheet 4e.

Seventh Embodiment

Crimping Process of the Front Surface Sheet 4f

Figure 5:
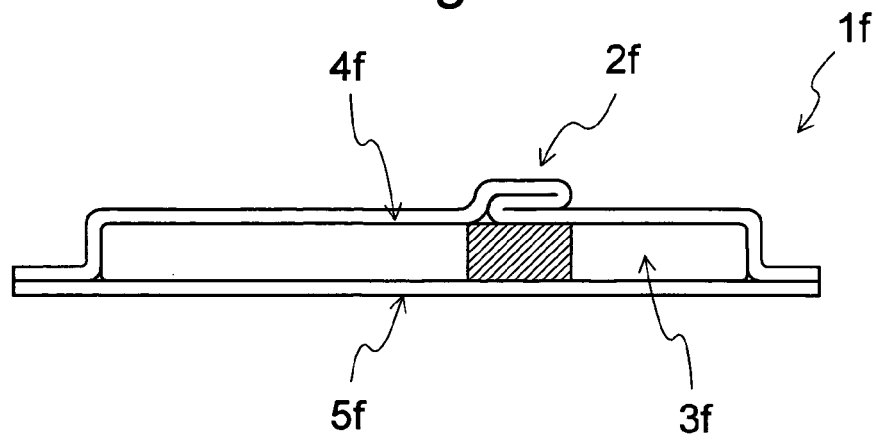
FIG. 5 is a cross-sectional view when cut in the longitudinal direction of the interlabial pad 1f according to a seventh embodiment.

The interlabial pad 1f of the seventh embodiment is one which uses a sheet which has been crimped as a front surface sheet 4e so that the front surface sheet 4f can expand in the central folding axis direction in the low flexural rigidity part 2f, and constituents excluding this are the same as those in the first embodiment. A part of the front surface 4f positioned on the low flexural rigidity part 2f can be enabled to stretch in the central folding axis direction X by being folded so as to form crimps in the direction perpendicular to the central folding axis (refer to FIG. 5) or corrugating to form grooves in the direction perpendicular to the central folding axis. When forming crimps by folding a part of the front surface sheet 4f, the width of the crimp is preferably 1 mm or more, and if it is narrower than 1 mm, sufficient stretching cannot be attained when the pad is bent in the central folding axis direction X. In addition, when corrugating, it is preferable that a distance of 0.5 to 3 mm be provided between the grooves and the depth of the groove of 0.1 to 3 mm.

Eigth Embodiment

Joining Stretchable Material to the Front Surface Sheet 4g

Figure 6:
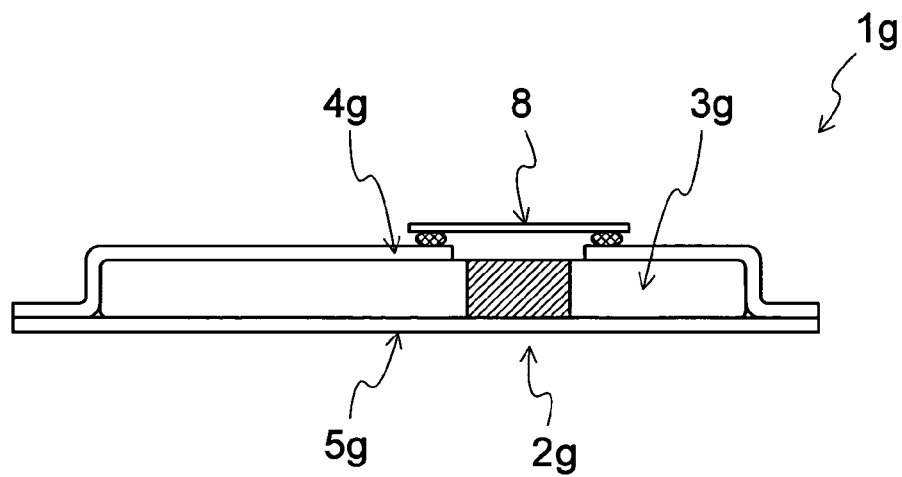
FIG. 6 is a cross-sectional view when cut in the longitudinal direction of the interlabial pad 1g according to an eight embodiment.

The interlabial pad 1g of the eighth embodiment is one in which material 8 which can be stretched in the central folding axis direction X is joined to a part of the front surface sheet 4g positioned in the low flexural rigidity part 2g, and constituents excluding this are the same as that in the first embodiment (refer to FIG. 6). Stretchable material can be selected from the materials described above.

Ninth Embodiment

Low Flexural Rigidity Part 2h of the Back Surface Sheet 5h

Figure 7:
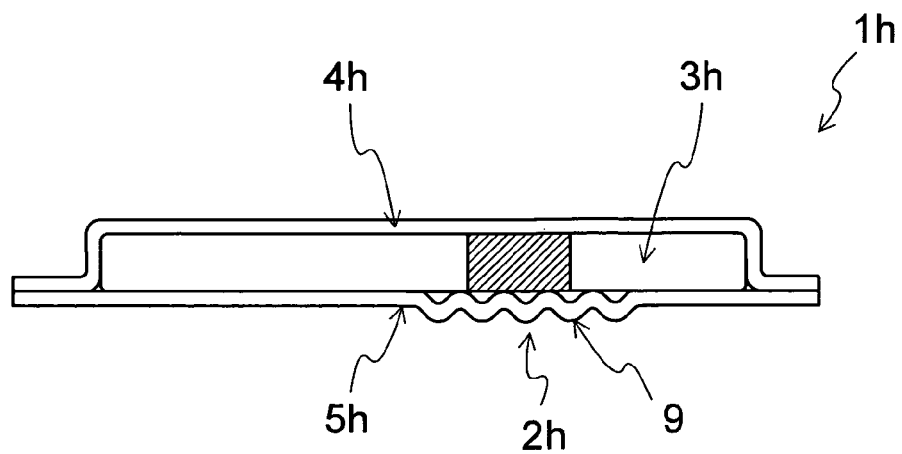
FIG. 7 is a cross-sectional view when cut in the longitudinal direction of the interlabial pad 1h according to a ninth embodiment.

The interlabial pad 1h of the ninth embodiment is one in which corrugating process which enables stretching in the central folding axis direction X is performed on a part of the back surface sheet 5h positioned in the low flexural rigidity part 2h, and constituents excluding this are the same as the first embodiment (refer to FIG. 7). It is preferable that the back surface sheet 5h positioned in the low flexural rigidity part 2h has expansibility in at least the central folding axis direction X, in order to not obstruct the bending of the interlabial pad 2h in the low flexural rigidity part 2h in the central folding axis direction X. As a method for giving expansibility, other than corrugating processing in which grooves are formed in the direction perpendicular to the central folding axis (refer to FIG. 7), methods such as cutting broken lines, cutting out in a circle, and opening holes, are given. When giving the back surface sheet 5h fluid-hydrophilic properties, corrugating processing 9 is preferable. In addition, when the pad is folded and used such that the front surface sheet is convex, the expansibility of the back surface sheet can be lower than the front surface sheet. In the back surface sheet, the crimps formed by corrugating processing and the like are preferably stretched with no resistance, and the stress is preferably 0 N/25 mm or more and 1.5 N/25 mm or less when stretched 3% in the central folding axis direction. If stress is larger than 1.5 N/25 mm, the back sheet is stretched and obstructs bending when the pad is bent in the central folding axis direction.

Tenth Embodiment

Cut Out Portion

The interlabial pad 1i, according to the tenth embodiment, is composed of a front surface sheet 4i, a back surface sheet 5i, and an absorbent member 3i placed therebetween, and a cut out portion 20i which extends toward the central folding axis from the side-edges along the central folding axis of the pad, but does not reach the central folding axis, is provided. The pudendal slit appears to bend on the surface according to the changes in the position (for example, walking, sleeping positions, etc.) In other words, the pudendal slit appears to bend on the surface because the tip part of the labia minora moves slightly in a horizontal direction, accompanying the changes in the position. However, even when the pudendal slit appears to bend, the vestibular floor within the labia normally maintains a straight line without bending. The tenth embodiment enables the tip of the pad in the vertical direction to bend according to the slight bend of the labia without deflecting the central folding axis.

Figure 8:
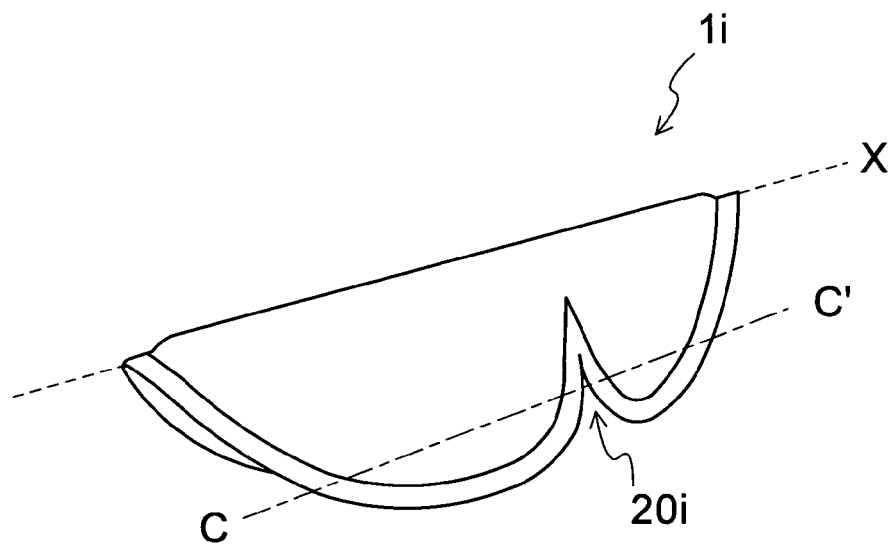
FIG. 8 is a perspective view of an interlabial pad 1i according to a tenth embodiment, which is folded into two.
Figure 9:
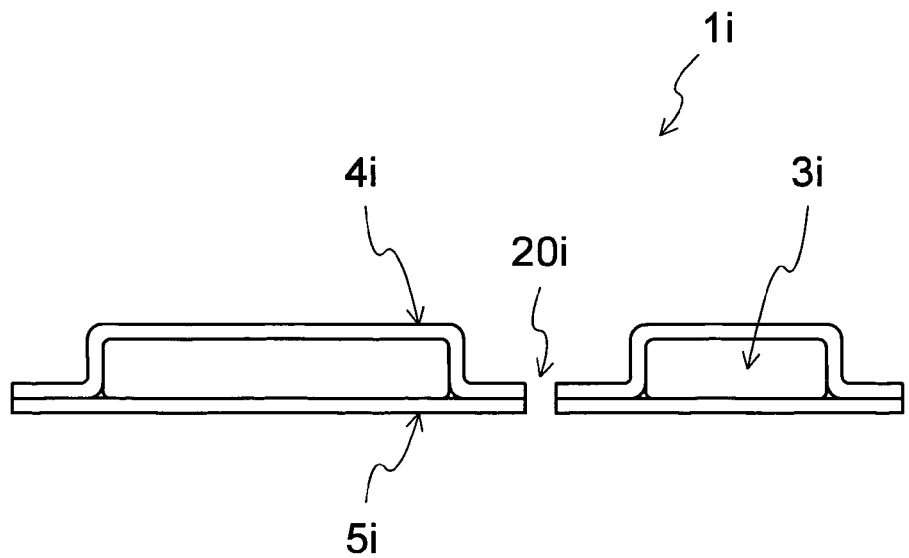
FIG. 9 is a C-C' cross-sectional view of the interlabial pad 1i in FIG. 8.

FIG. 8 is a perspective view of the interlabial pad li according to the tenth embodiment. In addition, FIG. 9 is a C-C' cross-sectional diagram of FIG. 8. The interlabial pad 1i according to the tenth embodiment has the cut out portion 20i which extends toward the central folding axis from the side-edges along the central folding axis of the pad, but does not reach the central folding axis. Therefore, the side-edges of the pad are separated in the central folding axis direction, into a front part and a back part. The cut out portion 20i extending toward the central folding axis from the side-edges, along the central folding axis, is formed such that the distance from the central folding axis is preferably 3 to 20 mm and more preferably 5 to 10 mm. If the distance from the central folding axis is shorter than 3 mm, the pad is cut into two pieces in the central folding axis direction X, and it becomes difficult to maintain the shape of pad 1i. On the other hand, if it is longer than 20 mm, the center line is not bent because the movable range of the pad 1i is too narrow, and it becomes difficult to enable the central folding axis of the pad 1i to come into contact with the vestibular floor within the labia.

Because the effects of pressure applied from the outside differ with the front part of the pad 1i tucked into the labia minora and the back part of the pad 1i exposed from the labia minuora, the vicinity of the ostium vaginae contact part becomes the cause of bending. Therefore, it is preferable that the position for placing the cut out portion be in the vicinity of the ostium vaginae.

Modified Example of the Tenth Embodiment

Figure 10:
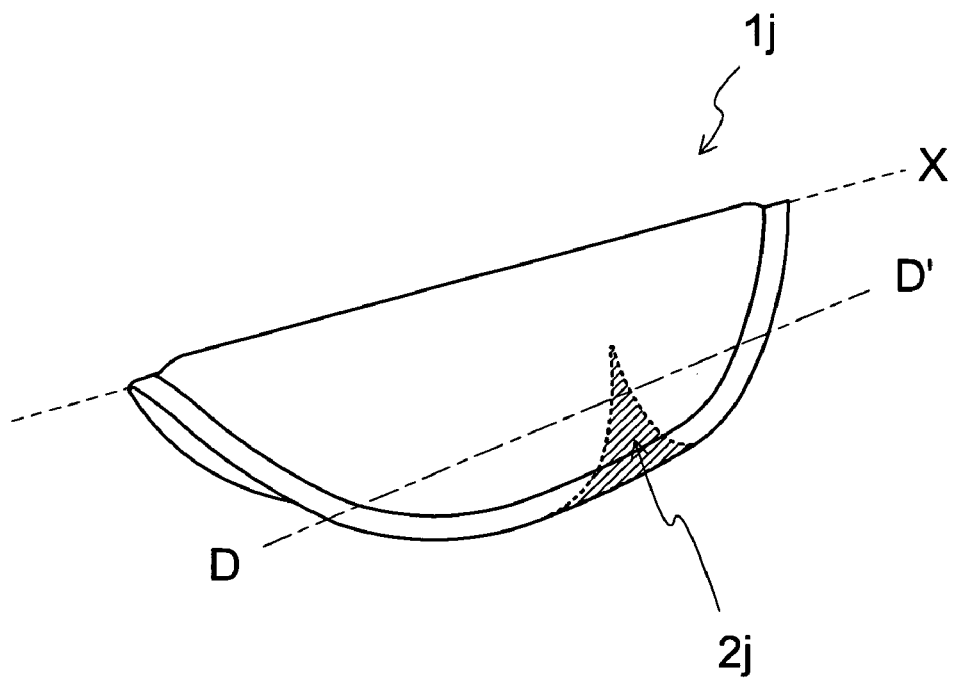
FIG. 10 is a perspective view of an interlabial pad 1j according to a modified example of the tenth embodiment, which is folded into two.
Figure 11:
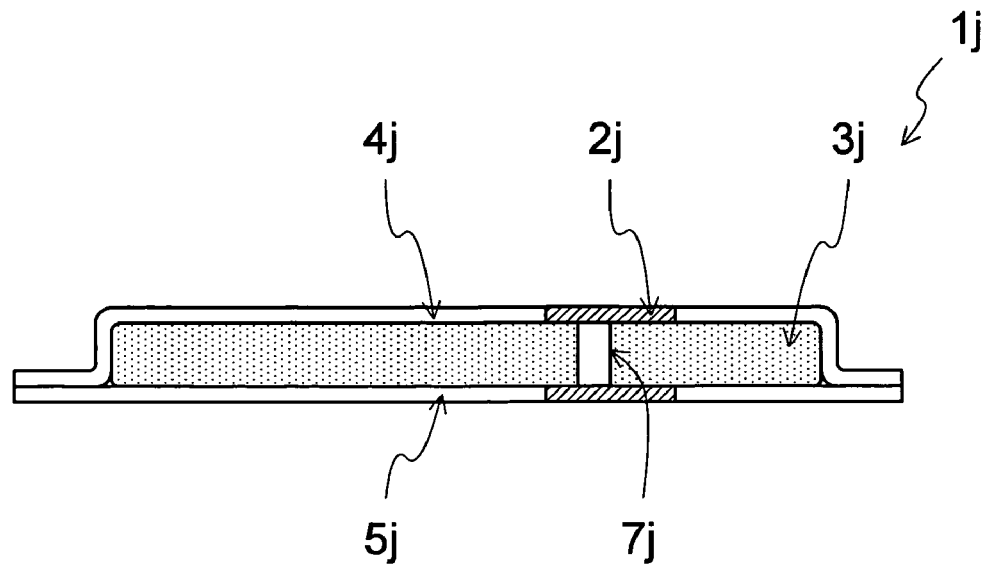
FIG. 11 is a D-D' cross-sectional view of the interlabial pad 1j in FIG. 10.

FIG. 10 is a perspective view of an interlabial pad 1j according to a modified example of the tenth embodiment. In addition, FIG. 11 is a D-D' cross-sectional view of FIG. 10. In the interlabial pad 1j according to the modified example of the tenth embodiment, a part of the side edge of an absorbent member 3j is cut, and the front surface sheet 4j and the back surface sheet 5j are not cut. As shown in FIG. 11, a cut portion 7*j* is provided on the absorbent member 3*j* by cutting a part of the absorbent member 3*j*. Parts of the front surface sheet and the back surface sheet covering the cut portion 7*j* are included of stretchable material or material which has been processed to allow expandability, preferably 1 mm or more or more preferably within the range of 3 to 10 mm in the central folding axis direction X, with the cut portion 7*j* as the center. If the parts of the front surface sheet and the back surface sheet to be stretchable are smaller than 1 mm from the cut portion 7*j* of the absorbent member 3*j*, the front surface sheet 4*j* and the back surface sheet 5*j* are pulled when the tip in the vertical direction of the interlabial pad when in use is bent in opposing directions according to the front part and back part of the pad, and it becomes difficult to bend freely. As stretchable material the same materials as in the first embodiment, for example, can be given.

Figure 12:
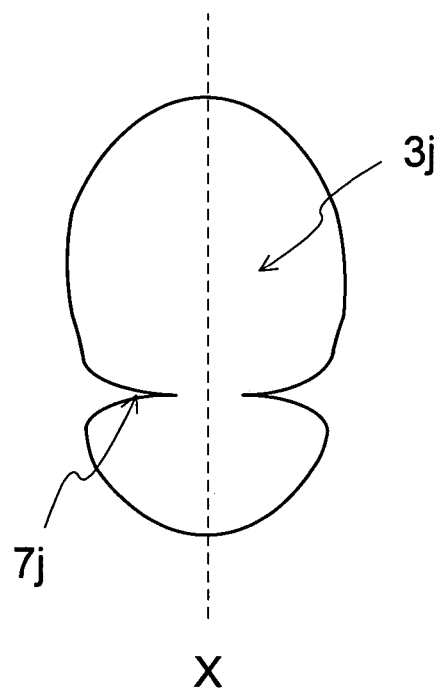
FIG. 12 is a top view of an absorbent member 3j in the modified example of the tenth embodiment.

FIG. 12 is a top view of an absorbent member 3*j* in a modified example of the tenth embodiment. The cut portion 7*j* formed by cutting a part of the absorbent member 3*j* extends towards the central folding axis from the side-edges along the central folding axis such that the distance from the central folding axis is preferably 2 to 20 mm and more preferably 5 to 10 mm. If the distance from the central folding axis is shorter than 2 mm, the pad is cut into two pieces in the central folding axis direction X, and it becomes difficult to maintain the shape of the absorbent member. On the other hand, if it is longer than 20 mm, the center line is not bent because the movable range of the pad 1*i* is too narrow, and it becomes difficult to enable the pad to remain placed along the vestibular floor within the labia.

Figure 13:
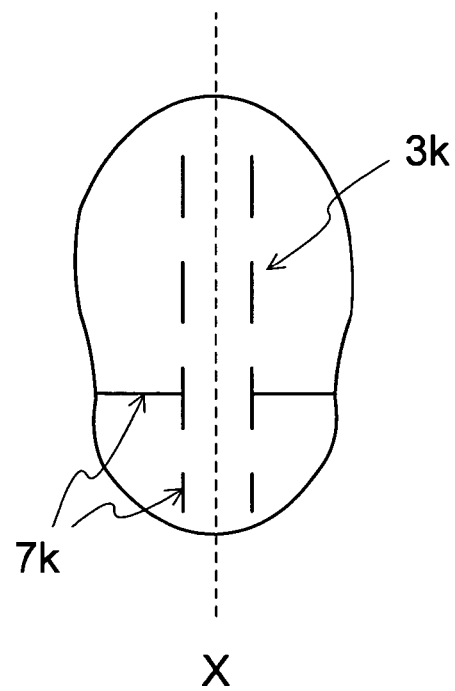
FIG. 13 is a top view of an absorbent member 3k in a modified example of the tenth embodiment.

FIG. 13 is an example of a more preferable absorbent member 3*k* in a modified example of the tenth embodiment. Slits 7*k* are provided in the absorbent member 3*k* and some of the slits 7*k* extend towards the central folding axis from the side-edges along the central folding axis such that the distance from the central folding axis is preferably 3 to 20 mm and more preferably 5 to 10 mm. The width of another slit 7*k* provided in the central folding axis direction X is preferably 1 to 20 mm and more preferably 5 to 10 mm, from the perspective of both causing shape retention and bending. In addition, the width of the part without a slit is preferably 1 to 20 mm and more preferably 5 to 10 mm.

Functions and Effects of the Tenth Embodiment

In the interlabial pad 1*i* according to the tenth embodiment, the tip in the vertical direction of the front part and the back part of the pas during wear can bend in differing horizontal directions by cutting a part of the absorbent member towards the central folding axis from the side-edges along the central folding axis of the absorbent member so that the tip of the cutting portion does not reach the central folding axis. Therefore, the central folding axis of the pad can maintain the form of a straight line, even if the tip part of the labia minora moves horizontally with the changes in the position of the wear and the front part and the back part of the pad are slightly bent in differing horizontal directions. At the same time, the tip in the vertical direction of the pad can bend with a slight bending of the labia. In addition, because the central folding axis of the pad can maintain the form of a straight line, a state in which the central folding axis of the pad is in contact with the vestibular floor within the labia in the form of a straight line can be maintained, and furthermore, because the tip part in the vertical direction of the pad can bend horizontally according to the slight bending of the labia, gaps are not formed between the inner walls of the labia and the pad, and close contact between the labia and the pad can be maintained. As a result, falling away of the pad from the labia can be prevented and menstrual blood will not leak from the gap.

Modified Example 1 of the First Embodiment to the Tenth Embodiment

Figure 14:
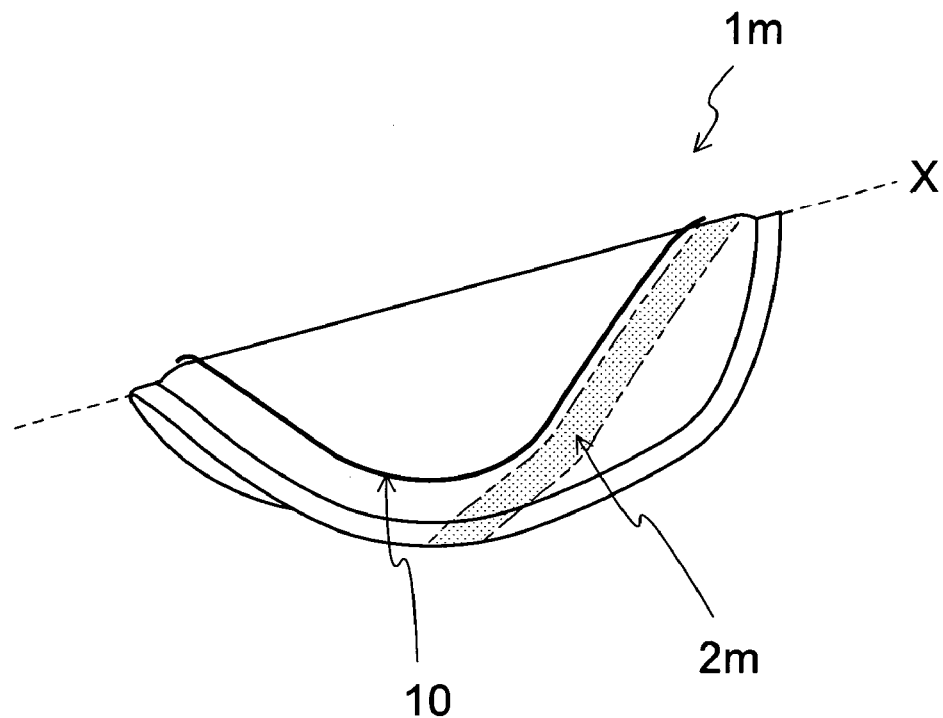
FIG. 14 is a perspective view of an interlabial pad 1m in modified example 1 of first to tenth embodiments, which is folded into two.
Figure 15:
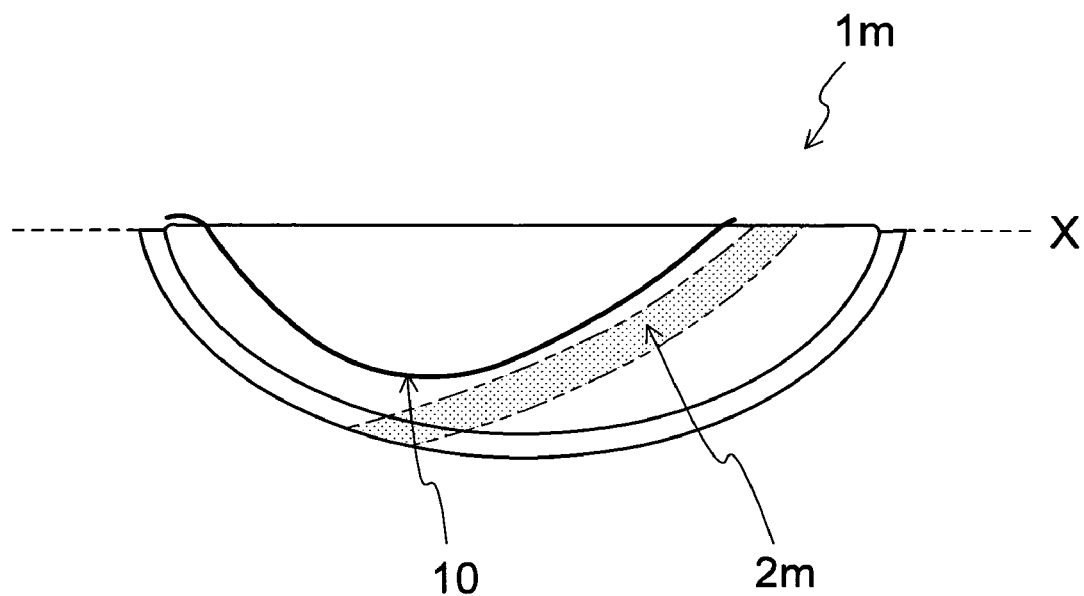
FIG. 15 is a view of the interlabial pad in FIG. 14 when seen from the side.

FIG. 14 is a perspective view of an interlabial pad 1*m* according to a modified example 1 of the first to tenth embodiments, and FIG. 15 is a view of this seen from the side. In the modified example 1 of the first to tenth embodiments, the low flexural rigidity parts in each embodiment are provided slanted to the front side of the wearer, at an angle of 10° or more and 90° or less to the central folding axis. More specifically, the low flexural rigidity part 2*m* in this modified example 1 is provided to strip-shaped areas, along an outline 10 tracing the outline of labia minora, slating to the front side of the wearer preferably at an angle of 20° or more and 80° or less and more preferably at an angle of 30° or more and 60° or less, towards the side-edges along the central folding axis from the central folding axis.

In most cases, the female labia minora is more developed in the vertical direction in the front part of the wearer than the back part, and while pad part which is tucked between the labia minora is held therewithin, external pressure directly affects the pad part which is exposed from the labia minora. By enabling the low flexural rigidity part 2*m* to be placed along the outer border of the labia minora, a region which preferentially bends can be provided between the borders of the part tucked between the labia minora and the part exposed from the labia minora, and this can cause bending.

Modified Example 2 of the First Embodiment of the Tenth Embodiment

In most cases, the female labia minora is more developed in the vertical direction in the front part than the back part. Therefore, when the interlabial pad is worn, the interlabial pad is easily exposed from the labia minora in the vicinity of the ostium vaginae and behind. As a result, the effects of external pressure to the front part of the pad which is tucked between the labia minora and the back part of the pad which is exposed from the labia minora differ, and the back part of the pad which is exposed from the labia minora tends to bend more easily in the central folding axis direction X, compared to the front part. Thus, a configuration in which the width measurement in the direction perpendicular to the central folding axis of the pad becomes smaller the further back it is, following the shape of the labia minora, is given as an alternate configuration. By reducing the width measurement in the direction perpendicular to the central folding axis of the back part of the pad rather than the front part, the amount of materials of the back part can be made less than the front part and the back part can be bent more easily.

Figure 16:
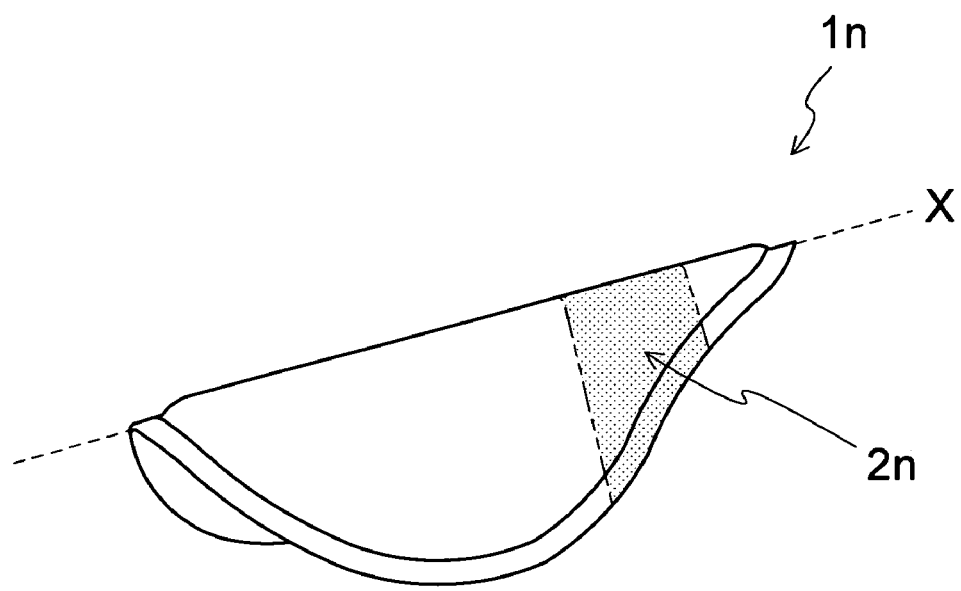
FIG. 16 is a perspective view of an interlabial pad in in modified example 2 of first to tenth embodiments, which is folded into two.
Figure 17:
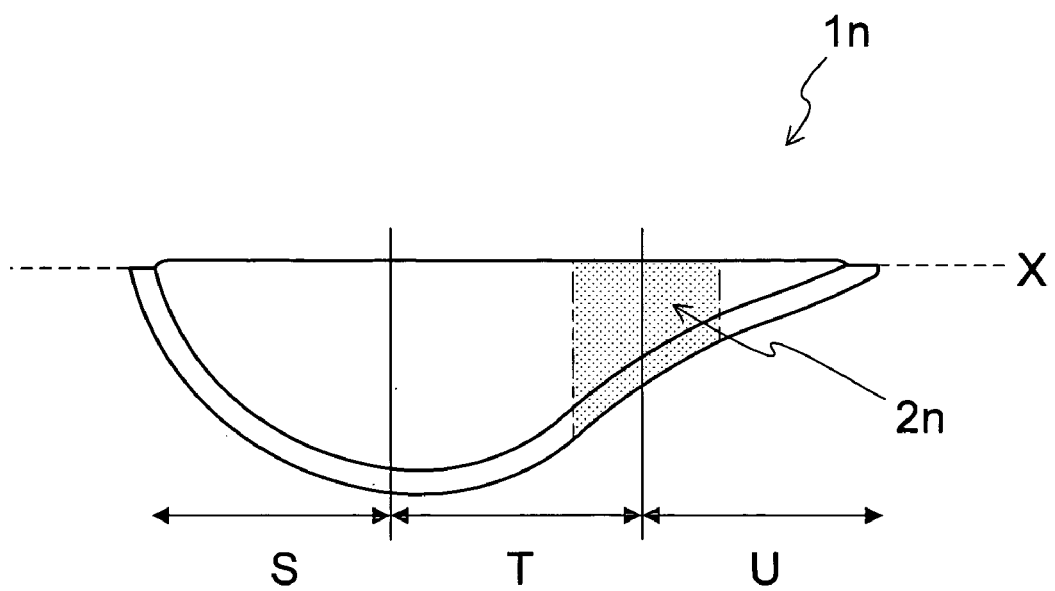
FIG. 17 is a view of the interlabial pad in FIG. 16 when seen from the side.

FIG. 16 is a perspective view of an interlabial pad 1*n*, according to the modified example 2 in the first to tenth embodiment, which is folded into two, and FIG. 17 is a view of this seen from the side. The total length of the outer form of the interlabial pad 1*n* is preferably 40 to 180 mm and more preferably 80 to 120 mm in the central folding axis direction X. If the length of the central folding axis of pad 1*n* is divided into three equal parts, from the front, front region S, center region T and back region U, it is preferable that the maximum width measurement from the front region S to the center region T be within the range of 50 to 80 mm. In addition, the width measurement at the border of the center region T and the back region U are preferably ⅔ to ½ of the maximum width. The width measurement indicated here is the measurement of a flattened interlabial pad 1*n* before being folded into two. When in use between the labia folded into two, the total length in the vertical direction in the worn form is about ½ of the above width. Although the interlabial pad in shown in FIG. 16 and FIG. 17 are the types in which a flattened pad is folded into two and held between the labia, it can also take on a bar-shape or a cylindrical shape. In pads other than the type in which a flattened pad is folded into two and worn, the width measurement is about ½ of the above width measurement.

In addition, the thickness of the pad in the direction horizontal to the body when held between the labial is preferably 4 to 12 mm and more preferably 6 to 8 mm. Furthermore, the measurement in the vertical direction when in use is more than the thickness of the pad and preferably ⅔ of the maximum width measurement or less. If the measurement in the vertical direction when in use is smaller than the thickness of the pad, it bends more easily in the direction perpendicular to the body, rather than horizontal, and on the other hand, if the measurement is larger than ⅔ of the maximum width measurement of the pad, the pad cannot bend easily.

Functions and Effects of the Modified Example 2 of the First Embodiment to the Tenth Embodiment In the modified example 2, by making the width measurement in the direction perpendicular to the central folding axis of the pad smaller the further back it is, following the shape if the labia minora, the amount of materials of the back part of the pas which is easily exposed from the labia minora becomes smaller than the amount of materials of the front part of the pad, and as a result, the pad can bend more easily in the central folding axis direction X in the back part rather than the front part. In addition, because the pad can bend easily and preferentially in the central folding axis direction X in the back part, which is easily exposed from the labia minora, the pad can be prevented from buckling and bending the labia and excessively stimulating the inner walls of the labia, and a gap forming between the pad and the inner walls of the labia, the pad falling away, and leakage occurring can be prevented.

What is claimed is:

1. An elongated interlabial pad comprising:
   a liquid-permeable surface side sheet;
   a back face sheet; and
   an absorbent member placed between said liquid-permeable surface side sheet and said back face sheet for absorbing and retaining body fluid; wherein:
   a central folding axis extends along a longitudinal centerline of said interlabial pad,
   the absorbent member includes a pair of first low flexural rigidity parts, each first low flexural rigidity part including a slit or cut out portion so that the first low flexural rigidity part has a lower flexural rigidity than areas of the absorbent member surrounding the first low flexural rigidity parts, the slit or cut out portion extending toward said central folding axis from a side-edge of the absorbent member,
   a basis weight per unit area in the first low flexural rigidity parts is less than a basis weight per unit area in the surrounding areas, such that the difference in basis weights per unit area is 20 g/m² or more and 1000 g/m² or less,
   the liquid-permeable surface side sheet includes a pair of second low flexural rigidity parts, each second low flexural rigidity part including a stretchable material or a material which has been processed to allow expandability and has a lower flexural rigidity that areas of the surface side sheet surrounding the second low flexural rigidity parts, each of said second low flexural rigidity parts overlapping each of said first low rigidity parts, extending from a side edge of the surface side sheet and having a larger extent in a direction parallel to said central folding axis near the side edge of the surface sheet than between the side edge of the surface side sheet and said central folding axis, and
   the back face sheet includes a pair of third low flexural rigidity parts, each third low flexural rigidity part including a stretchable material or a material which has been processed to allow expandability and has a lower flexural rigidity that areas of the back face sheet surrounding the third low flexural rigidity parts, each of said third low flexural rigidity parts overlapping each of said first low rigidity parts, extending from a side edge of the back face sheet and having a larger extent in a direction parallel to said central folding axis near the side edge of the back face than between the side edge of the back face sheet and said central folding axis.

2. The interlabial pad according to claim 1, wherein the slit or cut out portions are configured as strip-shaped areas that are provided at a slant from said central folding axis towards a front-side of said interlabial pad, at an angle of 10 degrees or more and 90 degrees or less to said central folding axis.

3. The interlabial pad according to claim 1, wherein said absorbent member comprises a pair of first parts each of which is positioned in each of said first low flexural rigidity parts and a second part positioned outside of said first low flexural rigidity parts; wherein the value of flexural rigidity B of each of said first parts is smaller than the value of flexural rigidity B of said second part; and wherein the difference is $0.1 \times 10^{-4}$ (Nm²/m) or more and $5.0 \times 10^{-4}$ (Nm²/m) or less.

4. The interlabial pad according to claim 1, wherein said absorbent member comprises fibers, a pair of first parts each of which is positioned in each of said first low flexural rigidity parts, and a second part positioned outside of said first low flexural rigidity parts; and wherein 5% or more fibers comprised in said first part have larger fiber diameters than fiber diameters of fibers comprised in said second part.

5. The interlabial pad according to claim 1, wherein embossing treatment is performed on said absorbent member, wherein said absorbent member comprises a pair of first parts each of which is positioned in each of said first low flexural rigidity parts and a second part positioned outside of said first low flexural rigidity parts; wherein the embossed-area ratio of said first part is smaller than the embossed-area ratio of said second part, and wherein the difference is 0.5% or more and 40% or less.

6. The interlabial pad according to claim 1, wherein the stress of said liquid permeable surface side sheet in said second low flexural rigidity part is 0.01 N/25 mm or more and 0.5 N/25 mm or less when stretched 5% in the direction roughly parallel to said central folding axis, when stretched with gripping interval of 100 mm and tensile rate of 100 m/mm.

7. The interlabial pad according to claim 6, wherein the stress of said back face sheet in said third low flexural rigidity part is 0 N/25 mm or more and 1.5 N/25 mm or less when stretched 3% in the direction of roughly parallel to said central folding axis, when stretched with gripping interval of 100 mm and tensile rate of 100 m/mm.

8. The interlabial pad according to claim 1, wherein said slit or cut out portion has a predetermined width and does not reach said central folding axis.

9. The interlabial pad according to claim 8, wherein said slit or cut out portion is provided only on said absorbent member.

10. The interlabial pad according to claim 8, wherein the second low flexural rigidity parts do not reach said central folding axis.

11. The interlabial pad according to claim 1, wherein the length from said central folding axis to said side-edge is smaller in the back-side of said interlabial pad than the front-side.

12. The interlabial pad according to claim 1, wherein a width of each second or third low flexural rigidity part is between 1 mm and 30 mm.

13. The interlabial pad according to claim 12, wherein the width of each second or third low flexural rigidity part is between 5 mm and 10 mm.

* * * * *